(12) United States Patent
Leshkov et al.

(10) Patent No.: US 9,265,743 B2
(45) Date of Patent: Feb. 23, 2016

(54) AGENT FOR INDUCING THE SYNTHESIS OF HEAT-SHOCK PROTEINS IN HUMAN AND ANIMAL CELLS

(71) Applicants: Sergey Yurievich Leshkov, Moscow (RU); Nina Sergeevna Vikhrieva, Moscow (RU)

(72) Inventors: Sergey Yurievich Leshkov, Moscow (RU); Nina Sergeevna Vikhrieva, Moscow (RU); Sergey Petrovich Krechetov, Moskovskaya obl. (RU)

(73) Assignees: Sergey Yurievich Leshkov, Moscow (RU); Nina Sergeevna Vikhrieva, Moscow (RU)

( * ) Notice: Subject to any disclaimer, the term of this patent is extended or adjusted under 35 U.S.C. 154(b) by 0 days.

(21) Appl. No.: 14/374,888

(22) PCT Filed: Jan. 22, 2013

(86) PCT No.: PCT/RU2013/000047
§ 371 (c)(1),
(2) Date: Jul. 25, 2014

(87) PCT Pub. No.: WO2013/115683
PCT Pub. Date: Aug. 8, 2013

(65) Prior Publication Data
US 2015/0065570 A1    Mar. 5, 2015

(30) Foreign Application Priority Data
Jan. 30, 2012    (RU) .................................. 2012102815

(51) Int. Cl.
| | |
|---|---|
| *A61K 31/194* | (2006.01) |
| *A61K 31/192* | (2006.01) |
| *A61K 31/07* | (2006.01) |
| *A61K 31/12* | (2006.01) |
| *A61K 31/122* | (2006.01) |
| *A61K 31/216* | (2006.01) |
| *A61K 31/355* | (2006.01) |
| *A61K 31/375* | (2006.01) |
| *A61K 8/36* | (2006.01) |
| *A61K 8/37* | (2006.01) |
| *A61Q 19/00* | (2006.01) |
| *A61K 8/86* | (2006.01) |
| *A61K 8/97* | (2006.01) |
| *A23L 1/30* | (2006.01) |
| *A23L 1/302* | (2006.01) |
| *A61K 36/74* | (2006.01) |
| *A61K 45/06* | (2006.01) |
| *A61K 47/10* | (2006.01) |
| *A61K 47/32* | (2006.01) |
| *A61K 47/44* | (2006.01) |

(52) U.S. Cl.
CPC ............... *A61K 31/194* (2013.01); *A23L 1/302* (2013.01); *A23L 1/3002* (2013.01); *A61K 8/36* (2013.01); *A61K 8/37* (2013.01); *A61K 8/86* (2013.01); *A61K 8/97* (2013.01); *A61K 31/07* (2013.01); *A61K 31/12* (2013.01); *A61K 31/122* (2013.01); *A61K 31/192* (2013.01); *A61K 31/216* (2013.01); *A61K 31/355* (2013.01); *A61K 31/375* (2013.01); *A61K 36/74* (2013.01); *A61K 45/06* (2013.01); *A61K 47/10* (2013.01); *A61K 47/32* (2013.01); *A61K 47/44* (2013.01); *A61Q 19/00* (2013.01); *A23V 2002/00* (2013.01)

(58) Field of Classification Search
CPC ... A61K 31/194; A61K 31/192; A23L 1/3002
USPC .................................. 514/533, 570; 435/375
See application file for complete search history.

(56) References Cited

U.S. PATENT DOCUMENTS

| | | | |
|---|---|---|---|
| 2002/0155097 A1* | 10/2002 | Tei ............................... | 424/93.7 |
| 2004/0167217 A1 | 8/2004 | Scapagnini et al. | |
| 2004/0228816 A1 | 11/2004 | Nizard et al. | |
| 2004/0234466 A1 | 11/2004 | Banowski et al. | |
| 2010/0068141 A1* | 3/2010 | Kaushal et al. ................ | 424/9.1 |
| 2010/0204093 A1* | 8/2010 | Kaushal et al. ................ | 514/12 |

FOREIGN PATENT DOCUMENTS

| | | |
|---|---|---|
| CN | 101 756 810 A | 6/2010 |
| DE | 699 28 005 T2 | 7/2006 |
| JP | S50 18621 A | 2/1975 |
| JP | 2007-230926 A | 9/2007 |
| WO | WO 2004/084854 A1 | 10/2004 |

OTHER PUBLICATIONS

Database GNPD 2007 "Rigenera Regenerating Night Cream" Database Accession No. 710319; XP-002731405.
Database GNPD 2010 "Cellular Anti-Ageing Intensive Serum" Database Accession No. 1469230; XP-002731406.
Database GNPD 2010 "Light Parisian Vanilla Ice Cream" Database Accession No. 1442459; XP-002731407.
Database GNPD 2009 "Mustard" Database Accession No. 1078209; XP-002731408.
Database GNPD 2010 "Curcumin OR100 Tablets" Database Accession No. 1384286; XP-002731409.
Database GNPD 2007 "Dietary Supplement" Database Accession No. 734756; XP-002731410.
Kato, K. et al. 1998 "Stimulation of the stress-induced expression of stress proteins by curcumin in cultured cells and in rat tissues in vivo" *Cell Stress & Chaperones* 3(3): 152-160.

* cited by examiner

*Primary Examiner* — Raymond Henley, III
(74) *Attorney, Agent, or Firm* — Knobbe, Martens, Olson & Bear, LLP

(57) ABSTRACT

An agent induces heat shock protein in human and animal cells. The agent includes at least one phenol compound that is a cinnamic acid derivative and at least one nonionic surfactant. The agent is useful in cosmetic preparations, food supplements and foodstuffs.

28 Claims, 7 Drawing Sheets

AGENT FOR INDUCING THE SYNTHESIS OF HEAT-SHOCK PROTEINS IN HUMAN AND ANIMAL CELLS

FIELD OF INVENTION

The present invention relates to the field of biology and medicine, in particular cosmetology, and can be used in creating and manufacturing cosmetic preparations, biologically active additives and foods.

PRIOR ART

Heat shock proteins (HSP) are a class of functionally similar proteins whose expression is induced in response to elevated temperatures and many other adverse exposures. By this time, several HSP families have been isolated differing in molecular weight. The expression of genes encoding heat shock proteins is regulated by heat shock factor (HSF), which under normal conditions exists in the form of an inactive monomer bound to HSP. That complex disintegrates following a heat shock or another stress, and heat shock factor forms trimers capable of binding to DNA and activating HSP transcription. Heat shock proteins have been found in the cells of virtually all living organisms ranging from bacteria to humans.

According to the present invention, HSPs are proteins that perform functions of molecular chaperones and participate in the folding of newly synthesized proteins and proteins with partially damaged structure. HSP participate in preventing the aggregation of incorrectly folded or partially unfolded proteins, assembly and disintegration of supramolecular protein structures, transport of proteins through membranes, and also unfolding of damaged proteins for their subsequent catabolism. HSP content increases in the cells of an organism subjected to elevated temperature or other stresses, as well as exposed to HSP inducing substances.

Out of the five defined HSP classes, of interest for the purposes of the present invention are HSP60, 70, 90, and 100, which possess the most intense chaperone function. The induction of the aforesaid HSPs is considered to be a defining factor for increasing stress resistance of cells.

The activation of HSP synthesis in the cells of an organism exposed to a stress factor disrupting its normal functioning, is considered now to be a protective reaction contributing to the enhancement of cell resistance to external stress and the removal of structural and functional proteins damaged by the stress/Heat Shock Proteins and Whole Body Physiology 1st Edition/. A. A. A. Asea and B. K. Pedersen (eds.), 2010, 430 p./.

Not only heating is among the factors, resistance to which is related to HSP expression. The induction of HSP synthesis has been demonstrated under exposure to cooling, intoxications, ultraviolet radiation, fasting, hypoxia, shortage of water, electrolyte imbalances, severe physical exertion, mechanical tissue damages, infections, and inflammatory reactions of any etiology. The action of the above external factors with intensity sufficient to cause disruption of cell functioning but not resulting in rapid irreversible damage (necrosis) of the cell and, consequently, the respective tissue, is described as stress.

Insufficient HSP synthesis in an organism is accompanied with a low cell growth rate and elevated apoptosis, and is a characteristic of cells of an aging organism. A clinically insufficient HSP synthesis is accompanied with poor healing of wounds, neurodegenerative diseases, elevated sensitivity of tissues of the organism to ischemia, and reproductive defects.

Purposeful cell HSP level regulation is contemplated as an opportunity to influence the sensitivity of a certain group of cells, a tissue, an organ or the organism in general to therapeutic action, exposure to harmful production factors or adverse environmental factors. Of practical interest are both HSP induction and inhibition.

Inhibition of HSPs is contemplated mainly as applied to therapeutic action on cancer cells. In this respect, a method is known of application of HSP inhibitors containing benzo[a]quinolizine tricyclic rings as a component of anti-cancer therapy with the use of hyperthermia as a way to sensitize cells to anti-cancer therapies being carried out/WO 2007/041294 2007/.

HSP induction is intended for wider application.

The use is known of biologically active substances inducing HSP synthesis for growing muscular mass/US 2011/0189312, 2011/. For that purpose, a composition is suggested that includes glutamine, creatine and substances inducing the production of heat shock proteins in cells.

The fact is known that an increased HSP level in cells is used to mitigate adverse consequences of hypoxia, hyperoxia, ischemia of tissues, high temperature, ultraviolet radiation, cytotoxic or radiation effects, metabolic disorders, or mechanical damage. For that purpose, hydroxylamine derivatives are used as components of cosmetic and pharmaceutical compositions/U.S. Pat. No. 7,148,239, 2006/.

It is known that acetylsalicylates are used as components of cosmetic or pharmaceutical compositions as agents capable of inducing HSP synthesis/US 20060148767, 2006/. The said compositions are recommended for use in treating dermatological diseases, cardiomyopathies, neuropathies, diabetes, ischemias, and degenerative diseases of the nervous system.

A disadvantage of all the compositions described above is the fact that increased HSP expression resulting from application thereof is observed only after stress, e.g. elevated temperature. Without the effect of a stress or damaging factor the rise in HSP expression in the above cases is insignificant, which considerably reduces the effectiveness of protection due to insufficient quantity of molecular chaperones in the cells at the outset of the damaging action. This is especially important under intensive exposures characterized by a high level of primary damage.

It needs to be noted that thanks to its chaperone functions, HSPs also play an important role in reparative processes. In biological systems, reparative processes mean regeneration of their damaged parts. Repair takes place in the case of regeneration of damaged biomacromolecules and supramolecular formations (membranes, fibrils, organelles), which are structural and functional cell elements. What happens is not a new macromolecule synthesized or a new sub-cell structure formed instead of the damaged one, but repair of the damaged portions of the existing molecule or structure. Mechanisms of the repair of damages in this case are based on the functioning of constantly active molecular damage repair systems in the cell, first of all DNA repair.

The use is known of phytoestrogens, isoflavones, procyanidol oligomers, anthocyanins, amino acids, oligopeptides, phytic acid and other calcium chelating agents and plant extracts containing the aforesaid substances, as components of cosmetic compositions for inducing regeneration processes in protecting human skin from harmful factors of the environment/US 20030138502, 2003/. A disadvantage of the suggested method is the fact that stimulation provided by the described cosmetic composition regarding the functioning of the reparative systems is not lasting and requires both preparatory treatment on the day before contact with the harmful factor in question, and treatment directly prior to the harmful action. That said, a rise in HSP expression is observed only after the action of the harmful factor in question (exhaust gas, tobacco smoke). Without such stress or damaging action, a rise in HSP expression is insignificant, which, as already noted, considerably impairs the effectiveness of protection.

At present, aggressive cosmetic procedures are widely used in cosmetic practices for skin rejuvenation, correction of skin development defects and suppressing excessive accumulation of subcutaneous fat, such procedures causing regulated damage of problematic tissue cells not exceeding the overall reparative capabilities of the tissue.

Such procedures are performed by way of applying physical or chemical factors capable of causing functional and/or structural disruptions in cells.

The applied limited damage of skin cells and tissues results, on the one hand, in the removal of old cells and cells incapable of regeneration and repair, and on the other hand, to the induction of growth and proliferation of stable cells possessing sufficient reparative potential, which ensures the repair of damages in tissues that have undergone the damaging action. Subsequently, young tissue is formed both in the damaged zones and in adjacent areas.

However, aggressive cosmetic procedures, as a rule, have serious side effects:

when using laser radiation and intense pulse light: acne, herpetic infection, erosion;

when applying low temperature treatment: reddening, hematoma formation and tenderness to touch; a tingling sensation in and/or numbness of the areas having undergone treatment;

following chemical pealing and microdermabrasion: the occurrence of a hyperpigmented spot and exacerbation of the herpetic skin disorder;

in electricity procedures: chromatopathy (skin pigmentation disorder);

in radiofrequency procedures: pain, skin reddening, edema, blisters;

in ultraviolet procedures: slowly dissolving serous or blood spots under the skin;

Thus, aggressive cosmetic procedures result in a higher rate of irreversibly damaged cells in the problematic tissue, in part for the reason of a low level of reparative processes related to the low HSP cell content. Therefore, regeneration of normal skin structure is retarded, while the probability of side effects grows.

For example, in conducting aggressive cosmetic procedures accompanied with the absorption of energy by the skin and heating thereof, the use is known of cosmetic compositions that include, as HSP synthesis inducing agents, heavy metals, salicylates, non-steroid anti-inflammatory preparations, nicotine, alcohol, PPAR-gamma agonists, caffeine or mixtures thereof. Application of such agents is recommended to be performed in advance or simultaneously with the start of heating/US 20080031833, 2008/.

The limitation of the suggested method is the fact that a required pre-requisite of effective enhancement of HSP expression is heating of the skin, which is brought about by the action of the device used in the cosmetic procedure. As a result, the application of the cosmetic compositions does not guarantee protection from possible side effects due to a low HSP level at the outset of the aggressive cosmetic procedure.

In conducting dermatological ultraviolet procedures, the use is known of compositions that contain as their additional components, agents inducing heat shock protein synthesis, such as e.g. acetylsalicylic acid, salicylic acid, zinc compounds (zinc sulfate, zinc L-carnosine)/US 20110269693, 2011/.

The limitation of the above compositions is the fact that the greatest induction of HSP is observed only in combination with a stress factor used in the procedure.

Thus, the search for an agent effectively inducing HSP without stress is a practical goal of high priority. The achievement thereof will provide an opportunity to enhance the resistance of cells, tissues and the organism in general to intensive and rapidly growing damaging stress, such as, in particular, aggressive cosmetic procedures, severe physical exertion, including athletic workouts, and work in adverse and harmful conditions disrupting normal functioning of the reparative systems of the body.

SUMMARY OF INVENTION

It is the task of this invention to create an agent ensuring the most intensive possible heat shock protein (HSP) synthesis in human and animal cells without the need for applying additional stress factor, and creation, on the basis of the said agent, of cosmetic preparations intended for stimulating reparative processes and reducing side effects of aggressive cosmetic procedures; creation, on the basis of the said agent, of a food supplement, a foodstuff, and a method to reduce side effects of aggressive cosmetic procedures.

DETAILED DISCLOSURE OF INVENTION

Figure 1:
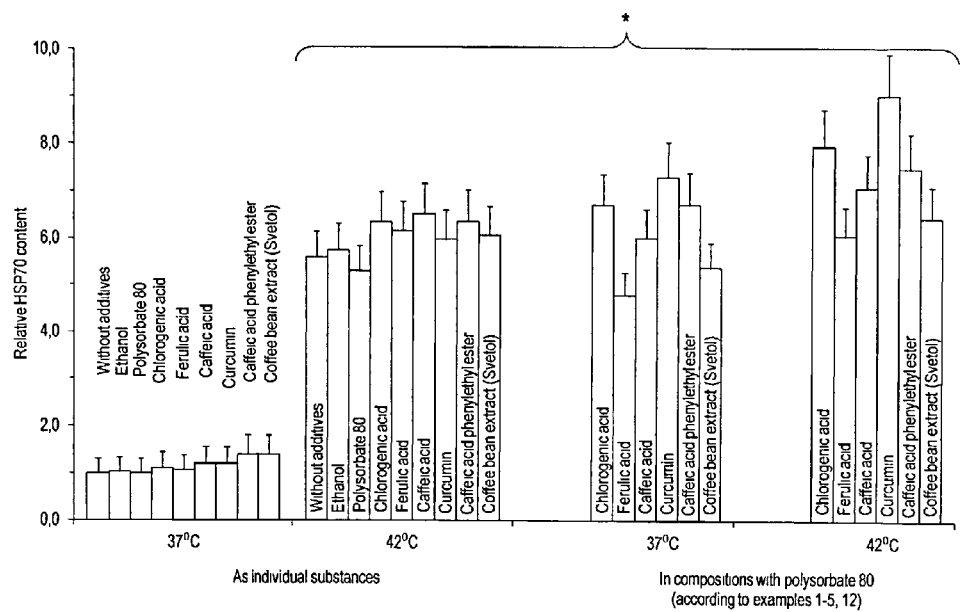
FIG. 1. HSP70 synthesis in human keratincytes after 4 hours of incubation at 37° C. and 42° C. (heat shock) in the presence of cinnamic acid derivatives after the addition of compounds to the culture medium as components of compositions with Polysorbate 80 and in the form of water (chlorogenic acid, coffee bean extract Svetol®) or alcohol (ferulic acid, caffeic acid, curcumin, the phenylethyl ester of caffeic acid) solutions.

To achieve the goal, an agent is proposed to induce heat shock protein synthesis in human and animal cells, comprising at least one phenol compound selected out of the group of cinnamic acid derivatives or a mixture of such compounds, and a nonionic surfactant or a mixture of such substances in an amount of at least 75 weight %.

Wherein, it is preferable that such cinnamic acid derivatives are chlorogenic, ferulic or caffeic acid, curcumin or the phenylethyl ester of caffeic acid.

Wherein, it is preferable that the mixture of phenol compounds is represented by an extract of raw materials of plant or animal origin.

Wherein, it is preferable that, as a plant extract, coffee bean extract is used, preferably green coffee bean extract.

Wherein, it is preferable that the nonionic surfactant is selected out of the group of substances with a hydrophilic-lipophilic balance (HLB) of from 10 to 18.

Wherein, it is preferable that Polysorbate 20, Polysorbate 40, Polysorbate 60, Polysorbate 80, PEG-40 hydrogenated castor wax, 35-polyoxyethylated castor oil or PEG-15 hydroxystearate is used as such nonionic surfactant.

Also disclosed herein is a cosmetic preparation for stimulating reparative processes, comprising a heat shock protein synthesis inducing agent comprising at least one phenol compound selected out of the group of cinnamic acid derivatives or a mixture of such compounds, and a nonionic surfactant or a mixture of such substances in an amount of at least 75 weight %.

Wherein, it is preferable that it contain a heat shock protein synthesis inducing agent in an amount of at least 0.1%, preferably from 0.5 to 5%.

Wherein, it is preferable that it additionally contain ascorbic acid or derivatives thereof in an amount of 0.01-20 weight %.

Wherein, it is preferable that it additionally contain a natural or synthetic fat-soluble antioxidant or a mixture of such antioxidants in an amount of 0.01-2 weight %;

Wherein, it is preferable that, as a natural or synthetic fat-soluble antioxidant, tocopherol, carotin, retinol, lutein, lycopin, ubiquinone or their derivatives are used.

Wherein, the cosmetic preparation may be in the form of emulsion, cream, milk, balm, ointment, gel, shampoo, tonic, lotion, or pomade.

Also disclosed herein is a cosmetic preparation for reducing side effects of aggressive cosmetic procedures, comprising a heat shock protein synthesis inducing agent comprising at least one phenol compound selected out of the group of cinnamic acid derivatives or a mixture of such compounds, and a nonionic surfactant or a mixture of such substances in an amount of at least 75 weight %.

Preferably, it contains a heat shock protein synthesis inducing agent in an amount of at least 0.1%, preferably from 0.5 to 5%.

Wherein, it is preferable that it additionally contain ascorbic acid or derivatives thereof in an amount of 0.01-20 weight %.

Wherein, it is preferable that it additionally contain a natural or synthetic fat-soluble antioxidant or a mixture of such antioxidants in an amount of 0.01-2 weight %;

Wherein, it is preferable that, as a natural or synthetic fat-soluble antioxidant, tocopherol, carotin, retinol, lutein, lycopin, ubiquinone or their derivatives are used.

Wherein, the cosmetic preparation may be in the form of emulsion, cream, milk, balm, ointment, gel, shampoo, tonic, lotion, or pomade.

Also disclosed herein is a method of reducing side effects of aggressive cosmetic procedures, comprising the performance of such procedures with the application of a cosmetic preparation on the skin at the place of such procedures for the purpose of reducing side effects of aggressive cosmetic procedures, wherein the agent is applied before and/or during and/or after the performed procedures.

Also disclosed herein is a food supplement, comprising a heat shock protein synthesis inducing agent comprising at least one phenol compound selected out of the group of cinnamic acid derivatives or a mixture of such compounds, and a nonionic surfactant or a mixture of such substances in an amount of at least 75 weight %.

Wherein, it is preferable the food supplement contain a heat shock protein synthesis inducing agent in an amount of at least 1%.

Wherein, it is preferable that it additionally contain ascorbic acid or derivatives thereof in an amount of 0.01-20 weight %.

Wherein, it is preferable that it additionally contain a natural or synthetic fat-soluble antioxidant or a mixture of such antioxidants in an amount of 0.01-2 weight %;

Wherein, it is preferable that, as a natural or synthetic fat-soluble antioxidant, tocopherol, carotin, retinol, lutein, lycopin, ubiquinone or their derivatives are used.

Wherein, such food supplement may be in the form of capsules, tablets, powder, granules, microspheres, pills, candy, suspension, emulsion, or solubilizate.

Also disclosed herein is a foodstuff, comprising a heat shock protein synthesis inducing agent comprising at least one phenol compound selected out of the group of cinnamic acid derivatives or a mixture of such compounds, and a nonionic surfactant or a mixture of such substances in an amount of at least 75 weight %.

Wherein, it is preferable that it contain a heat shock protein synthesis inducing agent in an amount of at least 0.001%, preferably from 0.01 to 0.5%.

Wherein, it is preferable that it additionally contain ascorbic acid or derivatives thereof in an amount of 0.01-20 weight %.

Wherein, it is preferable that it additionally contain a natural or synthetic fat-soluble antioxidant or a mixture of such antioxidants in an amount of 0.01-2 weight %.

Wherein, it is preferable that, as a natural or synthetic fat-soluble antioxidant, tocopherol, carotin, retinol, lutein, lycopin, ubiquinone or derivatives thereof are used.

Wherein, the foodstuff may be in the form of a ready-for-consumption product, instant food, food concentrate or beverage.

Also disclosed herein is a method of reducing side effects of aggressive cosmetic procedures, comprising the performance of such procedures accompanied by the consumption of a food supplement or foodstuff before and/or during and/or after the performed procedures.

Multiple literary and patent sources reviewed by the authors show that there is a variety of substances inducing heat shock protein synthesis in the cell. Wherein, as demonstrated by the author's research, of the greatest interest are natural phenol compounds that derive from phenolic acids.

Natural phenol compounds are produced by extraction from biogenic raw material of a plant or animal origin, and also synthetically, semi-synthetically and biotechnologically. Their chemical composition is quite diverse. Phenolic acids, flavonoids, polyphenol amines and mixed structure polyphenols are identified as principal representatives of natural phenol compounds.

In plants, phenol compounds are in a free state or in the form of glycosides. Possessing most diverse biological properties, they are capable of influencing many physiological processes in the human organism. Phenol compounds have long since found their use in medicine, where they are valued for their adaptogenic, stimulating and spasmolytic action;

they are used in treating neuroses and coronary failure. Phenol compounds possess diuretic, sedative, choleretic and hemostatic action.

The ability to stimulate synthesis (induce) HSP in mammalian cells has been discovered in natural phenol compounds that belong to derivatives of phenolic acids, namely benzoic and cinnamic acids.

The use is known of natural polyphenols related to phenolic acids that are cinnamic acid derivatives, which are capable of inducing neuroprotective peptides, including HSP, to protect cells of the central and peripheral nervous systems from degradation and perishing during degenerative diseases, injuries, age-related changes and other diseases or disorders/ US 20040167217, 2004/. However, by themselves, the said compounds are characterized by the ability to stimulate synthesis of HSP only against the background of the effect of damaging factors, which makes it possible to use them to suppress apoptosis of nervous cells only in non-acute pathological processes, among them degenerative diseases, age-related nervous system changes, post-traumatic inflammatory and ischemic conditions of the nervous system.

However, prior administration of the said compounds into the organism does not ensure a sufficiently high HSP level at the time of damaging action (stress). The needed HSP level is reached only in some time following the outset of such action. That results in massive accumulation of damaged molecules and is accompanied by a high proportion of irreversibly damaged cells, especially in the case of rapidly growing and intense damaging action.

Having conducted multiple experiments and research, the authors have found out that the inclusion of natural polyphenols selected out of the group of cinnamic acid derivatives into the structure of nonionic surfactant (NIS) micelles, such as Polysorbates and ethoxylated castor oil, results in high HSP induction levels both in vitro and in vivo.

Wherein, the obtained agent of NIS with cinnamic acid derivatives is self-emulsifying and is characterized by high bioavailability of biologically active substances in its composition.

A "self-emulsifying agent" means a substance on the basis of a surface-active agent (surfactant), which when added to a disperse medium forms a stable dispersion in technological procedures with moderate stirring. The self-emulsifying properties of the agent ensure high bioavailability of biologically active substances used therein in a variety of methods of administration to the organism, and makes it convenient to include the agent in a variety of cosmetic products, pharmaceuticals and foodstuffs. Wherein, it is preferable that surfactants with a HLB of 10-18 be used. For cosmetic, food and pharmaceutical purposes, a preference has been given lately to nonionic surfactants, for the reason of low toxicity thereof.

The discovered ability of cinnamic acid derivatives as components of NIS micelles to strongly induce HSP without additional stress makes it possible to consider the agent with the above-said composition as promising for stimulating reparative processes and increasing resistance of cells of the organism to intense and rapidly growing types of stress. The list of intense and rapidly growing types of stress includes, without limitation, aggressive cosmetic procedures, hard physical exertions, including athletic workouts, and also a variety of works under adverse and harmful conditions.

Wherein, by restoring native conformation of denatured proteins, HSPs ensure high efficiency of all processes lying in the foundation of regeneration (repair) of damaged biomacromolecules and supramolecular cell structures formed by the same. At the same time, HSPs, by interaction with the damaged proteins unable to regenerate, induce their catabolism in the cell with the formation of amino acids for the re-synthesis of new proteins.

To stimulate reparative processes and reduce side effects of aggressive cosmetic procedures, the suggested agent can be used as a component of cosmetic preparations, food supplements and foodstuffs.

The claimed method of reducing side effects of aggressive cosmetic procedures comprises application of cosmetic preparation and/or consumption of a food supplement or foodstuff containing the claimed HSP inducing agent before, during and after the aforesaid procedures.

The term "aggressive cosmetic procedures" means cosmetic procedures wherein the effect of physical or chemical factors is used capable of causing functional and/or structural disruptions in the cell. The limited cell and tissue damage applied in such procedures, not exceeding their compensatory capabilities, contributes to the activation of processes resulting in skin rejuvenation and restoration of its normal structure.

The list of aggressive cosmetic procedures wherein application of the claimed agent will result in a rise of efficacy thereof and lessening of accompanying undesirable effects, includes, without limitation, laser fractional photothermolysis, laser pealing, photoepilation, photorejuvenation, photo-removal of pigment spots, photo-removal of telangiectasias and other procedures carried out with the help of laser radiation or intense pulse light, hypo- (crio-) and hyperthermal dermatologic procedures, electroepilation and other electrical procedures, radiofrequency procedures, ultrasound cleansing and other ultrasound procedures, microdermabrasion, mechanical cleansing, chemical pealing and others.

The application of cosmetic preparation containing the claimed HSP inducing agent, and/or consumption of food supplements or foodstuffs containing the same, before and during the course of aggressive cosmetic procedures, as well as in the course of the subsequent period of restoration, allows to not only reduce the number of side effects intrinsic to such procedures, but also reduce the duration of such restorative period.

To produce the disclosed agent, the following substances are used acceptable for cosmetic, pharmaceutical or food purposes:
  at least one phenol compound selected out of the group of cinnamic acid derivatives or a mixture thereof in an amount of from 0.1 to 25 weight %;
  a nonionic surfactant, preferably with a hydrophilic-lipophilic balance (HLB) of from 10 to 18, or a mixture of such substances, in an amount of from 75 to 99.9 weight %.

As cinnamic acid derivatives, chlorogenic, ferulic or caffeic acid, curcumin or the phenylethyl ester of caffeic acid is used. However, the above list shall not limit the use of other cinnamic acid derivatives. The use of the above-mentioned compounds in the invention claimed herein supposes the possibility of their being found as components in extracts from raw materials of a plant or animal origin. As an example of such extract, not limiting the possibility of using other extracts, may serve a decaffeinated coffee bean extract enriched in a mixture of chlorogenic acid with other hydroxycinnamic acids (ferulic acid and caffeic acid). Extracts with the highest chlorogenic acid content are obtained from green coffee beans.

The invention disclosed herein uses micelle-forming NIS with a HLB of 10-18, possessing high solubilization capacity. Such compounds, without limiting the possibility to use other NIS for the purposes of the present invention, include Polysorbate 20, Polysorbate 40, Polysorbate 60, Polysorbate 80, PEG-40 hydrated castor oil (Cremophor RH 40), 35-polyoxyethylated castor oil (Cremophor EL), and PEG-15 hydroxystearate (Solutol HS 15).

To produce the claimed agent, the required amount of natural phenol compound or mixture of such compounds is dissolved in a NIS heated to 80° C. Depending on the NIS used, on cooling to room temperature a liquid transparent composition is obtained, or a paste-like opaque one which transforms in a transparent liquid on being heated to 30-40° C. The color of the obtained compositions is determined by the colors of components thereof.

The self-emulsifying nature of the compositions is demonstrated in the fact that, on adding such liquid compositions to water in an amount of up to 30 weight % at room temperature and stirring on a vortex mixer at 2,000 rpm for 30 seconds, a clear to weakly opalescent dispersion is formed stable at room temperature for a period of at least 3 months. For paste-like compositions, preparation of such dispersion should be performed at a temperature not lower than 35° C. and under the same stirring conditions. In that case, an opalescent disperse system is formed with storage stability of at least 3 months.

To produce a more stable agent with an increased HSP induction capacity, additional substances that are capable of reducing natural polyphenolic compounds and their oxygenated forms in animal and human cells, and also hydrophobic antioxidants, are added to the composition. It is preferable for the invention disclosed herein that, as agents reduced natural polyphenolic compounds, ascorbic acid and derivatives thereof (ascorbic acid salts, ascorbyl glucoside, ascorbyl palmitate, ascorbyl stearate) are used. The list of hydrophobic antioxidants used in the present invention includes tocopherol, carotin, retinol, lutein, lycopin, ubiquinone and their derivatives. The above lists do not limit the possibility to use other reductants and other hydrophobic antioxidants.

The agent suggested herein for heat shock protein induction in human and animal cells is obtained as follows.

A substance capable of reducing the said phenol compounds and their oxygenated forms in animal and human cells (e.g., ascorbic acid or derivatives thereof), in an amount of from 0.01 to 20 weight %, and a natural or synthetic fat-soluble antioxidant or a mixture of such antioxidants in an amount of 0.01-2 weight %, together with the necessary amount of natural phenol compound or a mixture of such compounds, are dissolved in an NIS heated to 80° C.; if all such substances being hydrophobic (fat-soluble). In case they are hydrophilic, a solution of hydrophilic compounds in water is first prepared at 80° C., and then that solution is mixed with a solution of hydrophobic antioxidant in a NIS. Water content of up to 10 weight % is allowed in the agent. Depending on the NIS used, on cooling to room temperature a liquid transparent composition is obtained, or a paste-like opaque one which transforms in a transparent liquid on heating to 30-40° C. The color of the obtained compositions is determined by the colors of components thereof.

Low content or absence of water in the claimed agent ensures stability of biologically active substances in the composition thereof for a long time. That, and the liquid or paste-like physical state of the agent claimed in the present disclosure at room temperature, renders it a convenient ingredient for the production of cosmetic preparations, food supplements, foodstuffs and pharmaceuticals. Besides, anhydrous embodiments of the agent are of interest for the production of goods wherein water as a component is unacceptable. For example, the agent may be used as a filler of soft gel capsules intended for use as food additives or medicinal products.

To produce cosmetic preparations for stimulating reparative processes and cosmetic preparations for reducing side effects of aggressive cosmetic procedures, the agent for heat shock protein induction in human and animal cells obtained as described above is added at any production stage.

In a preferred embodiment, the agent is added at the final stages of the production process of cosmetic preparations production at the temperature of 35-40° C. for paste-like, and at lower temperatures for liquid compositions. The self-emulsifying nature of the claimed agent allows to forgo intensive stirring to achieve effective dispersion of the agent in the product. Therefore, a uniform cosmetic product may be obtained in the form of emulsion, suspension, cream, milk, gel, ointment, balm, shampoo, tonic, lotion, or pomade. The claimed agent is compatible both with oil-in-water and water-in-oil cosmetic bases.

To ensure necessary bioactivity, the described cosmetic preparations will contain the claimed heat shock protein inducing agent in an amount of at least 0.1%, preferably from 0.5 to 5%.

To obtain a cosmetic product with an optimal manifestation of bioactivity, to the composition is added ascorbic acid or derivatives thereof in an amount of 0.01-20 weight % and/or natural or synthetic fat-soluble antioxidant or mixture of such antioxidants in an amount of 0.01-2 weight %. Tocopherol, carotin, retinol, lutein, lycopin, ubiquinone or their derivatives may be used as a natural or synthetic fat-soluble antioxidant.

Such cosmetic preparations may additionally contain a variety of biologically active substances, including those possessing moisturizing effect, regenerative action, ability to stimulate collagen synthesis, vitamins, cell growth factors and other ingredients of natural and chemical origin, permitted for use for cosmetic purpose.

In the production of a food supplement with the use of the claimed heat shock protein inducing agent, it is preferable that the greatest possible amount thereof be included in the composition of the food supplement. The use of less than 1% of the claimed agent is impractical, for it would be difficult to ensure an effective dose of the active ingredients.

In this connection, anhydrous embodiments of the heat shock protein inducing agent are of interest, which are applicable for filling up soft gel capsules with the greatest possible content of the agent. To produce suspensions, emulsions, solubilizates and candy, the claimed agent is added at any technological stage wherein, or whereafter, sufficiently prolonged but not necessarily intensive stirring is contemplated.

The preparation of granulated material containing the claimed agent using alcohol solutions thereof by means of wet granulation ensures the production of food supplements in the form of hard gel capsules, tablets, powders, granules, microspheres, and pills according to standard production processes for above dosage forms, with the use of respective auxiliary ingredients.

The production of food supplements containing the claimed agent is possible with that agent alone and in combination with other biologically active components.

Technological approaches described for the production of food supplements may also be used for the obtaining of a foodstuff product in the forms of a ready-for-consumption product, instant food, food concentrate or beverage. Taking into account that foodstuffs are consumed in great quantities, the content of the claimed agent therein should be lower than in food supplements. However, the content of the claimed agent in a foodstuff of less than 0.001% is impractical. Preferably, the claimed agent content in foodstuffs should be from 0.01 to 0.5%. The content of over 1% is permissible in food concentrates assuming dilution when consumed.

Methods of reducing side effects of aggressive cosmetic procedures using the heat shock protein inducing agent claimed herein are performed as follows:

before and/or during and/or after aggressive cosmetic procedures, a cosmetic preparation, which contains the claimed agent, is applied to the skin at the place of said procedures and/or the patient consumes a food supplement or foodstuff containing the claimed agent.

In superficial aggressive cosmetic procedures (laser fractional photothermolysis, laser pealing, photoepilation, photorejuvenation, photo-removal of pigment spots, photo-removal of telangiectasias and other procedures conducted with the help of laser radiation or intense pulse light, mechanical cleansing, chemical pealing), both combined and individual use of skin and oral application of the claimed agent is permissible.

In cases where the procedure in question involves deep skin layers and subcutaneous fat cells (hypo- (crio-) and hyperthermal dermatologic procedures, electrolysis and other electricity procedures, radiofrequency procedures, ultraviolet cleansing and other ultraviolet procedures, microdermabrasion), individual application is practicable only for peroral products containing the claimed agent.

A cosmetic preparation is applied on the skin surface in an amount of 0.05-0.2 g per cm² of skin surface to be treated in the course of the aggressive cosmetic procedure at hand. A food supplement or foodstuff should be administered in an amount containing from 1 to 15 mg of the claimed agent per kg of the body mass per day, preferably 2-10 mg/kg/day.

Taking into account the HSP induction time characteristics, the application of cosmetic products and/or administration of food supplements or foodstuffs containing the claimed agent should begin 1-3 days prior to aggressive cosmetic procedures. After the completion of said procedures, it is reasonable to continue the application of products containing the claimed agent in order to maintain the elevated level of reparative processes for several weeks till the completion of the rehabilitation period.

The administration of food supplements or foodstuffs containing the claimed agent described in the method of reducing side effects of aggressive cosmetic procedures also enables to lessen the extent of damage to muscular cells after hard physical exertions. Hard physical exertions include athletic workouts, various works under adverse and harmful labor conditions, and will not be limited with the cited list.

A food supplement or foodstuff is to be taken in that case in an amount containing from 1 to 15 mg of the claimed agent per kg of the body mass per day, preferably 5-10 mg/kg/day. The administration of said food supplement or foodstuff should be commenced 1-3 days prior to hard physical exertions and continued in order to maintain the elevated level of reparative processes for several weeks till the completion of the rehabilitation period.

The following examples illustrate the disclosed invention without limiting the scope thereof.

EXAMPLES

Examples 1-12

Various Options for NIS and Cinnamic Acid Derivative

To produce the agent, the necessary amount of NIS is heated to 80° C. After that, the needed amount of a cinnamic acid derivative is added in accordance with Table 1.

The mixture is stirred till complete dissolution of the added substance while maintaining the above indicated temperature. Then the prepared composition is cooled to room temperature and, depending on the NIS used, a clear liquid or opaque paste-like composition is obtained.

TABLE 1

| Ingredient | Ingredient content (gram) in example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Cinnamic acid derivative | | | | | | | | | | | | |
| Chlorogenic acid | 10.0 | | | | | 10.0 | 5.0 | 5.0 | 5.0 | 5.0 | 5.0 | |
| Ferulic acid | | 5.0 | | | | | | | | | | |
| Caffeic acid | | | 2.5 | | | | | | | | | |
| Curcumin | | | | 0.5 | | | | | | | | |
| Phenylethyl ester of caffeic acid | | | | | 1.0 | | | | | | | |
| Coffee bean extract (Svetol) | | | | | | | | | | | | 25.0 |
| NIS | | | | | | | | | | | | |
| Polysorbate 20 (Tween 20) | | | | | | 90.0 | | | | | | |
| Polysorbate 40 (Tween 40) | | | | | | | 95.0 | | | | | |
| Polysorbate 60 (Tween 60) | | | | | | | | 95.0 | | | | |
| Polysorbate 80 (Tween 80) | 90.0 | 95.0 | 97.5 | 99.5 | 99.0 | | | | | | | 75.0 |
| PEG-40 hydrated castor oil (Cremophor RH 40) | | | | | | | | | 95.0 | | | |
| 35-polyoxyethylated castor oil (Cremophor EL), | | | | | | | | | | 95.0 | | |
| PEG-15 hydroxystearate (Solutol HS 15) | | | | | | | | | | | 95.0 | |
| Obtained product state | L | L | L | L | L | L | P | P | P | P | P | L |

Note.
L—transparent liquid composition which, when mixed with water heated to 37° C., forms weakly opalescent solubilizate;
P—paste-like opaque composition turning into transparent liquid if heated to 35° C. Mixing of such liquid heated to 37° C. with water heated to the same temperature produces a strongly opalescent disperse system, stable at room temperature for at least 3 months.
Such compositions may be used in producing cosmetic preparations, food supplements and foodstuffs.

Example 13

Increasing HSP70 content in the cells of a keratincyte culture in vitro under the exposure to chlorogenic acid, ferulic acid, caffeic acid, curcumin, the phenylethyl ester of caffeic acid and coffee bean extract (Svetol) as components of compositions with Polysorbate 80 without additional exposure to a stress factor.

Keratincytes were obtained from skin samples collected from healthy volunteers having given their informed consent in the course of cosmetic interventions. Skin sections washed in PBS, with removed subcutaneous fat, were incubated overnight at 4° C. in a dispase-containing PBS solution. Thereafter, epidermis was separated from derma and placed in a solution containing trypsin and EDTA at 37° C. On completion of incubation, trypsin activity in the medium was suppressed by the addition of soybean trypsin inhibitor, and after resuspension, keratincytes were precipitated by means of centrifugation. The cells obtained thereby were cultivated in a serum-free medium for keratincytes with the addition of growth factors at 37° C. in culture flasks with 5% CO2. The medium was changed every 3-4 days. A day before the experiment, samples of $3 \times 10^5$ cells were put into the wells of 6-well plates.

To research the effect of substances and compositions on HSP production, the culture medium was removed from the wells, and each well was filled with 2.0 ml of mixture of complete medium for keratincytes, prepared in advance and heated to 37° C., containing compositions of cinnamic acid derivatives with Polysorbate 80 according to examples 1-5 and 12, or water solutions or, given poor solubility in water, alcohol solutions of cinnamic acid derivatives. Mixtures were prepared by adding the needed amount of solution or compositions, with subsequent stirring till obtaining a transparent dispersion or solution. The final concentrations in incubation medium were: for cinnamic acid derivatives—50 µM, for coffee bean extract—50 µg/ml, for Polysorbate 80—max. 0.25%, for ethanol—max. 0.05%. Control wells contained in an incubation medium of 0.25% Polysorbate 80 or 0.05% ethanol.

After the addition of the above-described mixtures of the culture medium with substances and compositions under study, a portion of the plates were incubated for 4 hours at 42° C., and the rest at 37° C. for the same period of time. Following incubation, the incubation medium was removed from the wells, cells detached from substrate with a Versen solution and washed three times with PBS by means of centrifugation. The obtained cell residue was lysed with a solution containing protease inhibitors in accordance with the sample preparation protocol for immunoferment analysis (ELISA). The HSP70 content in the obtained samples was determined by means of ELISA method.

FIG. 1 shows HSP70 synthesis in human keratincytes after 4 hours of incubation at 37° C. and 42° C. (heat shock) in the presence of cinnamic acid derivatives after the addition of said compounds to the culture medium as components of compositions with Polysorbate 80 and in the form of water (chlorogenic acid, coffee bean extract Svetol) or alcohol (ferulic acid, caffeic acid, curcumin, the phenylethyl ester of caffeic acid) solutions.

The relative HSP70 content calculates as ratio of absolute values in wells with specified conditions to mean absolute content of HSP70 in the wells without additions having undergone incubation at 37° C., and shows as mean plus/minus standard error of the mean for three experiments. *–P<0.05 in comparison with the values in samples without heat shock and addition of individual substances. Here and hereinafter the unpaired Student t-test is used.

The obtained results (FIG. 1.) demonstrate the ability of the claimed agent, comprising a phenol compound selected out of the group of cinnamic acid derivatives, or a mixture of such compounds, and a nonionic surfactant, to induce HSP70 synthesis without any additional exposure to stress to the level, similar to that, achieved under heat shock.

Example 14. Increasing HSP70 content in the cells of a fibroblast culture in vitro under the exposure to chlorogenic acid as a component of compositions with Polysorbate 20, Polysorbate 40, Polysorbate 60, Polysorbate 80, PEG-40 hydrated castor oil (Cremophor RH 40), 35-polyoxyethylated castor oil (Cremophor EL), PEG-15 hydroxystearate (Solutol HS 15) without additional exposure to stress.

A culture of the mouse fibroblast NIH/3T3 cell line was grown in the DMEM medium with the addition of L-glutamine, penicillin, streptomycin and 10% embryonic calf serum at 37° C., 5% CO2. Cell passaging was performed twice a week, till the monolayer reached 80-90% confluency. A day before the experiment, $3 \times 10^5$ cells were added to the wells of 6-well plates.

To research the effect of substances and composition on HSP production, the culture medium was removed from the wells, and each well was filled with 2.0 ml of complete DMEM medium-NIS mixture, prepared in advance and heated to 37° C., or their compositions with chlorogenic acid according to examples 6-11. Mixtures were prepared by adding the needed amount of NIS or compositions, with subsequent stirring till obtaining a transparent dispersion or solution. Prior to preparing culture medium mixtures with compositions according to examples 7-11 and the respective NIS, components of said mixtures were heated to 37° C. The final concentration of chlorogenic acid was 50 µM in all the wells containing the same. NIS concentration in the wells without chlorogenic acid was 0.035%.

After the addition of the above-described mixtures of the culture medium with substances and compositions under study, a portion of the plates were incubated for 4 hours at 42° C., and the rest at 37° C. for the same period of time. Following incubation, the incubation medium was removed from the wells, cells detached from substrate with a Versen solution and washed three times with PBS by means of centrifugation. The obtained cell residue was lysed with a solution containing protease inhibitors in accordance with the sample preparation protocol for immunoferment analysis (ELISA). The HSP70 content in the obtained samples was determined by means of ELISA.

Figure 2:
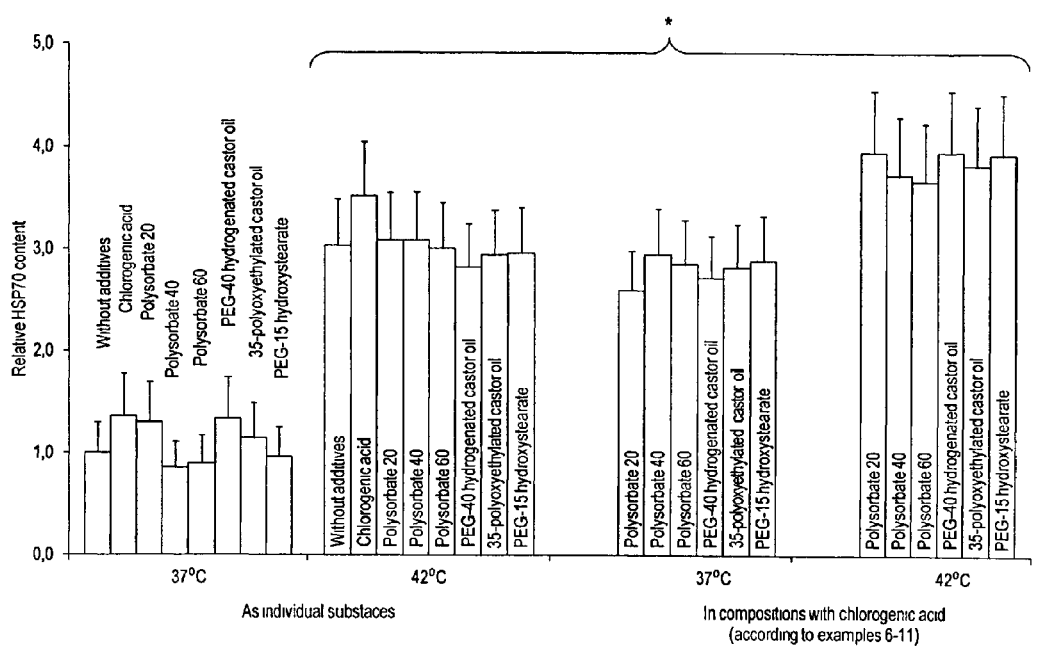
FIG. 2. HSP70 synthesis in NIH/3T3 line fibroblasts after 4 hours of incubation at 37° C. and 42° C. (heat shock) in the presence of chlorogenic acid under addition of the compounds in the culture medium as components of compositions with a variety of non-ionic surfactants (NIS) and in the form of water solution.

FIG. 2 shows HSP70 synthesis in NIH/3T3 line fibroblasts after 4 hours of incubation at 37° C. and 42° C. (heat shock) in the presence of chlorogenic acid under addition of the said compounds in the culture medium as components of compositions with a variety NIS and in the form of water solution.

The relative HSP70 content calculates as ratio of absolute values in wells with specified conditions to mean absolute content of HSP70 in the wells without additions having undergone incubation at 37° C., and shows as mean plus/minus standard error of the mean for three experiments. *–P<0.05 in comparison with the values in samples without heat shock and addition of individual substances.

The obtained results (FIG. 2) demonstrate the ability of the claimed agent, comprising a phenol compound selected out of the group of cinnamic acid derivatives, and one of a variety of nonionic surfactants, to induce HSP70 synthesis without any additional exposure to stress to the level, similar to that, achieved under heat shock.

Examples 15-23

Various Options for NIS and Cinnamic Acid Derivatives in Combination with Ascorbic Acid Derivative and Hydrophobic Antioxidant To produce the agent, the necessary amount of NIS is heated to 80° C. After that, the needed amount of a cinnamic acid derivative is added in accordance with Table 2. The mixture is stirred till complete dissolution of the added substance while maintaining the above indicated temperature. To the obtained transparent composition is added ascorbyl palmitate and hydrophobic antioxidant in quantities indicated in the table, and stirred till obtaining a transparent liquid. Then the prepared composition is cooled to room temperature and, depending on the NIS used, a clear liquid or opaque paste-like composition is obtained.

TABLE 2

| Ingredient | Ingredient content (gram) in example | | | | | | | | |
|---|---|---|---|---|---|---|---|---|---|
| | 15 | 16 | 17 | 18 | 19 | 20 | 21 | 22 | 23 |
| Cinnamic acid derivative | | | | | | | | | |
| Chlorogenic acid | 10.0 | 1.0 | | | | | | | |
| Coffee bean extract (Svetol) | | | 15.0 | 15.0 | 15.0 | 15.0 | 15.0 | 15.0 | 10.0 |
| NIS | | | | | | | | | |
| Polysorbate 80 (Tween 80) | 79.0 | | 74.0 | 74.95 | 74.975 | 74.75 | 74.75 | 74.5 | 78.95 |
| Polysorbate 60 (Tween 60) | | 93.5 | | | | | | | |
| Ascorbic acid derivative | | | | | | | | | |
| Ascorbyl palmitate | 10.0 | 5.0 | 10.0 | 10.0 | 10.0 | 10.0 | 10.0 | 10.0 | 10.0 |
| Fat-soluble antioxidant | | | | | | | | | |
| α-tocopherol | 1.0 | 0.5 | 1.0 | | | | | | 0.5 |
| β-carotin | | | | 0.05 | | | | | 0.05 |
| retinol | | | | | 0.025 | | | | |
| lutein | | | | | | 0.25 | | | |
| lycopin | | | | | | | 0.25 | | |
| ubiquinone | | | | | | | | 0.5 | 0.5 |
| Obtained product state | L | P | L | L | L | L | L | L | L |

Note.
L—transparent liquid composition which, when mixed with water heated to 37° C., forms weakly opalescent solubilizate;
P—paste-like opaque composition turning into transparent liquid if heated to 35° C. Mixing of such liquid heated to 37° C. with water heated to the same temperature produces a strongly opalescent disperse system, stable at room temperature for at least 3 months.
Such compositions may be used in producing cosmetic preparations, food supplements and foodstuffs.

Example 24

Preparing Agent: Polyphenol+ПАВ+Antioxidant+Ascorbic Acid+Water

To 69 g of Polysorbate 80 heated to 80° C. is added 1 g of α-tocopherol and 10 g of chlorogenic acid and stirred till obtaining a transparent composition. 10 g of ascorbic acid is dissolved in 10 g of water heated to 80° C. and added to a mixture of a polysorbate with an antioxidant. The mixture is stirred till obtaining a transparent composition and cooled to room temperature. A transparent liquid composition is obtained, which when mixed with water forms a transparent solubilizate. This composition may be used in producing cosmetic preparations, food supplements and foodstuffs.

Example 25

Preparing Agent: Antioxidant+ПАВ+Polyphenol+Ascorbic Acid+Water

To 78 g of Polysorbate 80 heated to 80° C. is added 1 g of α-tocopherol and stirred till obtaining a transparent composition. 1 g of chlorogenic acid and 10 g ascorbic acid are dissolved in 10 g of water heated to 80° C. and added to a mixture of a Polysorbate with an antioxidant. The obtained mixture is stirred till obtaining a transparent composition and cooled to room temperature. A transparent liquid composition is obtained, which when mixed with water forms a transparent solubilizate. This composition may be used in producing cosmetic preparations, food supplements and foodstuffs.

Example 26

Preparing Agent with Green Coffee Bean Extract+ПАВ+Ascorbic Acid+Antioxidant+Water To 77 g of Polysorbate 80 heated to 80° C. is added 1 g of α-tocopherol and stirred till obtaining a transparent composition. 2 g of green coffee bean extract and 10 g ascorbic acid are dissolved in 10 g of water heated to 80° C. and added to a mixture of a Polysorbate with tocopherol. The obtained mixture is stirred till obtaining a transparent liquid and cooled to room temperature. A transparent liquid composition is obtained, which when mixed with water forms a transparent solubilizate. This composition may be used in producing cosmetic preparations, food supplements and foodstuffs.

Example 27

Demonstration of more intense and stable increase of HSP70 content in fibroblast culture cells in vitro under the exposure of compositions of chlorogenic acid with a NIS, an ascorbic acid derivative and an antioxidant compared to the exposure of compositions of chlorogenic acid with just a NIS.

A culture of the mouse fibroblast NIH/3T3 cell line was prepared and got ready for experiments as described in example 14.

To research the effect of fibroblasts on HSP production, the culture medium was removed from the wells, and each well was filled with 2.0 ml of complete DMEM medium mixtures with compositions, or with solutions in said medium of substances comprised by such compositions, prepared in advance and heated to 37° C. Compositions according to examples 1 and 15 were used, as well as compositions of Polysorbate 80 with α-tocopherol and Polysorbate 80 with ascorbyl palmitate, which were obtained when mixed in proportions described in example 15. Mixtures were prepared by means of addition of the necessary amount of compositions or individual substances and subsequent stirring till obtaining a transparent dispersion or solution. The final concentration of substances added to the culture medium was: for chlorogenic acid—50 μM, for ascorbyl palmitate—42.7 μM, and for α-tocopherol—4.1 μM. The concentration of Polysorbate 80 in the incubation medium when added in the pure form was 0.016%, which corresponds to its greatest concentration when added as a component of compositions used.

After the addition of the above-described mixtures of the culture medium with substances and compositions under study, a portion of the plates were incubated for 1, 2, 3 or 4 hours at 37° C. and 5% CO2, while in another portion of the plates, mixtures under study were substituted, following 4 hours of incubation, for the complete DMEM medium and incubated for another 20 hours under the same conditions. Following each incubation version, the incubation medium was removed from the wells, cells detached from substrate with a Versen solution and washed three times with PBS by means of centrifugation. The obtained cell residue was lysed with a solution containing protease inhibitors in accordance with the sample preparation protocol for immunoferment analysis (ELISA). The HSP70 content in the obtained samples was determined by means of ELISA.

Figure 3:
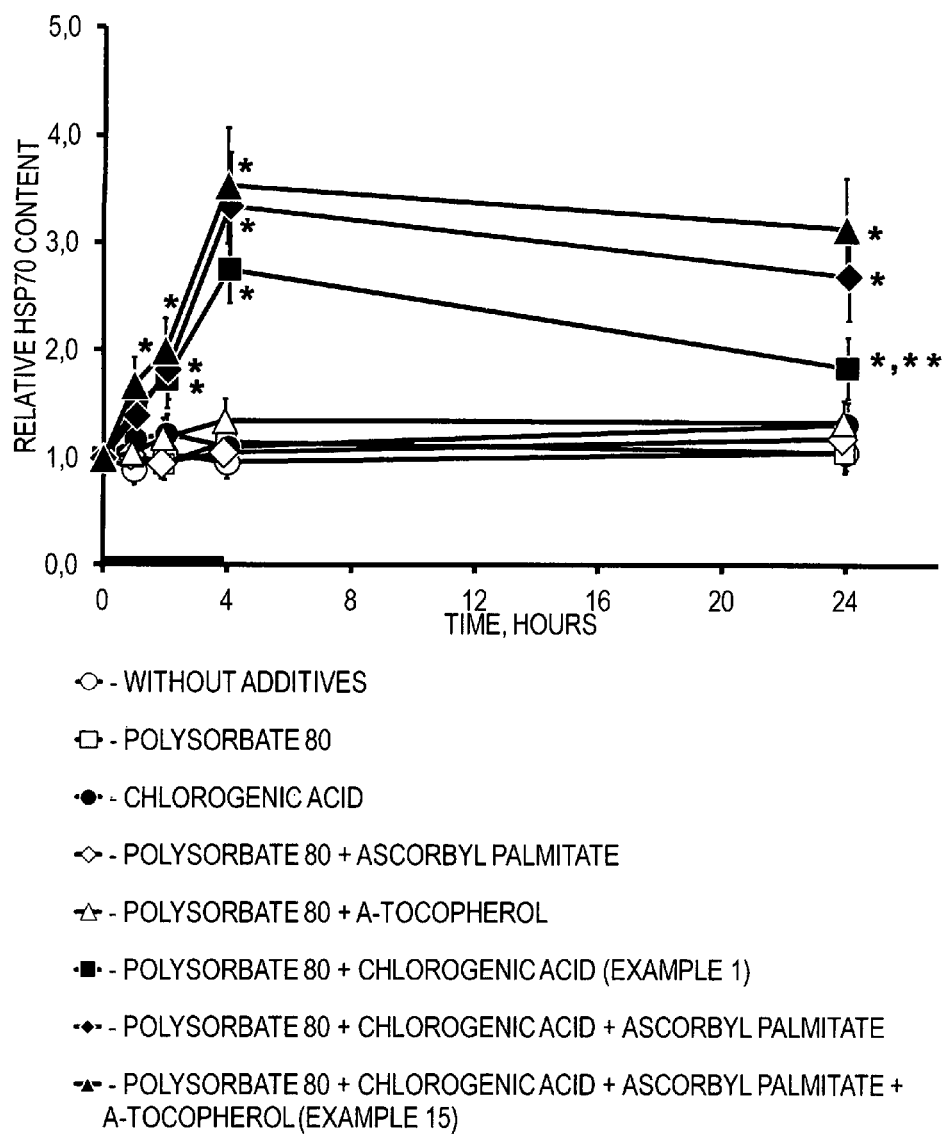
FIG. 3. HSP70 synthesis in NIH/3T3 line fibroblasts in the presence of chlorogenic acid and compositions thereof with an NIS, an ascorbic acid derivative and a hydrophobic antioxidant.

FIG. 3 shows HSP70 synthesis in NIH/3T3 line fibroblasts in the presence of chlorogenic acid and compositions thereof with an NIS, an ascorbic acid derivative and a hydrophobic antioxidant.

The relative HSP70 content calculates as ratio of absolute values after treatment to mean absolute content of HSP70 after the removal of the culture medium before treatment with additives, and shows as mean plus/minus standard error of the mean for three experiments. *–P<0.05 in comparison with the values prior to incubation with additives. **–P<0.05 in comparison with the values after 4 hours of incubation with additives. The period of incubation with additives is highlighted by a thickening of the horizontal axis.

The obtained results (FIG. 3) demonstrate a more expressed and better sustained HSP70 induction by the claimed agent if the latter comprises, beside a phenol compound selected out of the group of cinnamic acid derivatives, and a NIS, additionally an ascorbic acid derivative and a hydrophobic antioxidant.

Example 28

Demonstration of the Protective Action of the Claimed Agents on Fibroblast Culture Cells Exposed to Cytotoxic Action In Vitro A culture of the mouse fibroblast NIH/3T3 cell line was prepared and got ready for experiments as described in example 14, with the exception that 96-well plates were used, and 1×10$^5$ cells per well were added a day prior to experiment.

In the experiments, compositions according to examples 17-22 were used, said compositions being added to a complete DMEM culture medium in an amount of 0.02%, and a composition according to example 12, said composition added in an amount of 0.012%. Also, compositions were used of Polysorbate 80 with α-tocopherol and Polysorbate 80 with ascorbyl palmitate, said compositions obtained by mixing in proportions provided in example 17, and added to the culture medium in an amount corresponding to their content in wells if complete compositions of example 17 being added. Mixtures of compositions with the medium were prepared by means of addition of the needed amount of compositions or individual substances and subsequent stirring till the obtaining of a transparent dispersion or solution. The final concentrations of substances in the culture medium were: for green coffee bean extract (Svetol)—30 μg/ml, for ascorbyl palmitate—48.2 μM, and for α-tocopherol—4.6 μM. The concentration of Polysorbate 80 in the incubation mixture when added in the pure form was 0.015%, which corresponds to its greatest concentration when added as a component of compositions used.

To research the effect of HSP induction on fibroblast sensitivity to cytotoxic exposure, the culture medium was removed from the wells, and each well was filled with 0.2 ml of the above-described mixtures prepared in advance and heated to 37° C. After the addition, the plates were incubated for 4 hours at 37° C. and 5% CO2. After that, the mixture under study were substituted for 0.2 ml of the complete DMEM medium, or the complete DMEM medium containing 50 μM of sodium arsenate, and incubated for another 20 hours under the same conditions.

Following incubation, 20 μl of MTT (3-(4,5-dimethylthiazol-2-yl)-2,5-diphenyltetrazolium bromide) solution with concentration of 5 mg/ml in PBS was added to each well and incubated for 4 hours. Then the culture medium was completely removed, 200 μl of dimethylsulfoxide added to each well and mixed by way of intense shaking for 30 minutes. The amount of formazan generated, which is proportional to functional cell activity, was estimated by optical density of the well content on a plate photometer at 550 nm.

Figure 4:
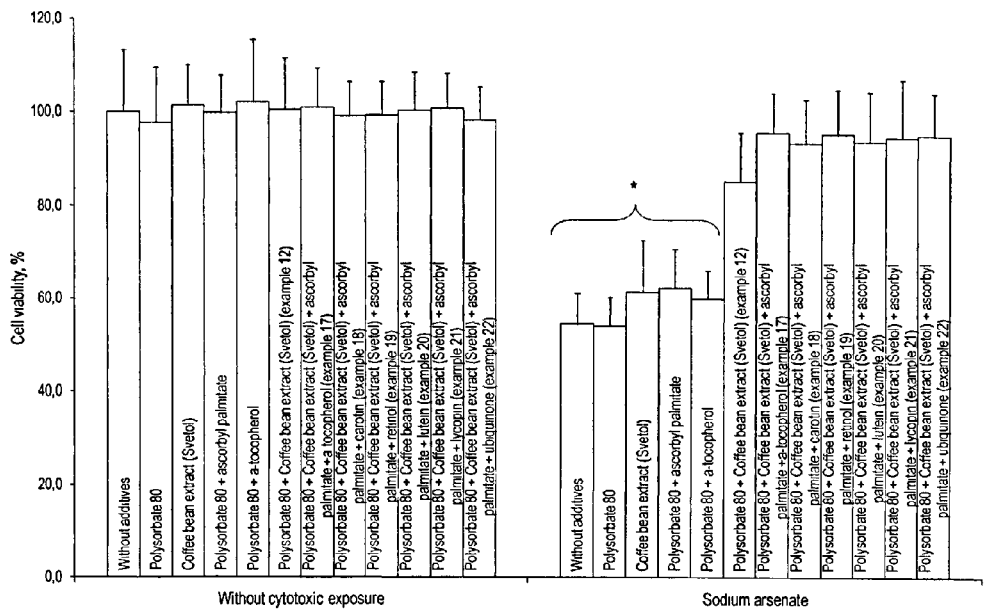
FIG. 4. NIH/3T3 line fibroblast viability in the presence of green coffee bean extract (Svetol®) compositions with an NIS, an ascorbic acid derivative and a hydrophobic antioxidant under toxic exposure.

FIG. 4 shows NIH/3T3 line fibroblast viability in the presence of green coffee bean extract (Svetol) compositions with an NIS, an ascorbic acid derivative and a hydrophobic antioxidant under toxic exposure. The cell viability in wells is characterized by a ratio of optical density of their content to the mean optical density of content of the wells without additions. The data is shown as the mean±standard error of the mean for three experiments. *–P<0.05 when compared to the values in wells with same additions of substances under study, or compositions thereof, without the cytotoxic exposure to 50 μM of sodium arsenate for 20 hours.

The obtained results (FIG. 4) demonstrate an expressed antitoxic effect of green coffee bean extract (Svetol) compositions with a NIS, an ascorbic acid derivative and a hydrophobic antioxidant. The effect of compositions comprising only green coffee bean extract and an NIS, is slightly lower. At the same time, green coffee bean extract in its pure form possesses weak antitoxic action.

Example 29

Preparing a Cosmetic Cream for the Stimulation of Reparative Processes with the Inclusion of the Claimed Agent As a cosmetic preparation used for stimulating reparative processes, cream of the following composition may be used:

| A | |
|---|---|
| Carbopol Ultrez 21 | 0.30% |
| Water | 53.34% |
| B | |
| Triethanolamine | 0.40% |

-continued

| C | |
|---|---|
| Arlamol E | 2.66% |
| Brij 721 | 1.99% |
| Brij 72 | 3.32% |

| D | |
|---|---|
| Water | 31.89% |

| E | |
|---|---|
| Composition according to example 16 (green coffee bean extract + NIS + ascorbyl palmitate + antioxidant) | 5.00% |

| F | |
|---|---|
| Germaben II | 1.00% |
| Fragrance | 0.10% |

To prepare the cream, a weight of Carbopol Ultrez 21 (Phase A) is dumped on the surface of water, allowing enough time for it to become fully wetted, and then stirred to uniformity. Triethanolamine is then added (Phase B) and stirred to uniformity (Phase AB). Arlamol E, Brij 721, Brij 72 (Phase C), water (Phase D) are heated to 85° C. Phase C is added to Phase D and homogenated on Ultra Turrax for 3 minutes till the formation of a uniform emulsion. Hot Phase CD is added to Phase AB and carefully mixed by propeller agitator. The mixture of Phases ABCD is allowed to cool to 40° C. under stirring. Following that, a composition according to example 16 (Phase E), Germaben II and fragrance (Phase F) are added to Phase ABCD. Stirring is continued till the cream achieves room temperature and uniform consistency is obtained. The obtained cream is stable for at least 12 months.

The above-described cream is applied to open skin areas exposed to harmful environmental factors, including harmful production factors. The cream may be used in the course of aggressive cosmetic procedures for stimulating rejuvenation and regeneration of the skin, as well as for the reduction of side effects of such procedures.

Example 30

Preparing a Cosmetic Cream for Stimulating Reparative Processes and Reducing Side Effects of Aggressive Cosmetic Procedures As a cosmetic preparation used for the stimulation of reparative processes and reduction of side effects of aggressive cosmetic procedures, in particular, cream of the following composition may be used:

| A | |
|---|---|
| Emulgade SE PF | 8.00% |
| Cetearyl alcohol | 5.00% |
| Avocado oil | 3.00% |
| Eutanol G | 3.00% |
| Dimethicone DM350 | 2.00% |
| Chamomile oil extract | 0.50% |

| B | |
|---|---|
| Water | до 100% |

| C | |
|---|---|
| Composition according to example 12 (green coffee bean extract + NIS + ascorbyl palmitate + antioxidant) | 3.00% |

| D | |
|---|---|
| D-panthenol 75% | 1.33% |
| Microcare DMP | 1.00% |
| Fragrance | 0.10% |

To prepare the cream, A is heated to 80° C. and stirred to uniformity. B is heated to 80° C., and A is added to B under intense stirring. Continuing stirring, the mixture is cooled down, adding components C and D on reaching 40° C. Stirring is continued till the cream reaches room temperature and uniform consistency is obtained. The obtained cream is shelf-stable for a period of at least 12 months.

The above-described cream is applied to the skin in the place of aggressive cosmetic procedures before, during and after said procedures, which results in the stimulation of skin rejuvenation and regeneration, as well as in the reduction of side effects of such procedures. The cream may be applied to open skin areas exposed to harmful environmental factors, including harmful production factors.

Example 31

Preparing a Cosmetic Cream for Reducing Side Effects of Aggressive Cosmetic Procedures As a cosmetic preparation used for the reduction of side effects of aggressive cosmetic procedures, in particular, cream of the following composition may be used:

| A | |
|---|---|
| Eusolex OCR | 9.00% |
| Emulgade SE PF | 8.00% |
| Cetearyl alcohol | 5.00% |
| Avocado oil | 3.00% |
| Eutanol G | 2.00% |
| Dimethicone DM350 | 2.00% |
| Eusolex 9020 | 2.00% |
| Vitamin E | 0.50% |
| Chamomile oil extract | 0.50% |
| Ascorbyl palmitate | 0.05% |

| B | |
|---|---|
| Water | до 100% |
| Beta-1,3-glucan | 0.50% |
| Allantoin | 0.20% |

| C | |
|---|---|
| D-panthenol 75% | 1.33% |
| Microcare DMP | 1.00% |
| Composition according to example 12 (green coffee bean extract + NIS) | 2.00% |
| Calmosensine ™ | 3.00% |

| D | |
|---|---|
| Fragrance | 0.10% |

To prepare the cream, A is heated to 80° C. and stirred to uniformity. Then B is prepared and heated to 80° C. A is added to B under intense stirring. Continuing stirring, the mixture is cooled down, adding components C and D on reaching 40° C. Stirring is continued till the cream reaches room temperature and uniform consistency is obtained. The obtained cream is shelf-stable for a period of at least 12 months.

The above-described cream is applied to the skin in the place of aggressive cosmetic procedures before, during and after said procedures, which results in the stimulation of skin rejuvenation and regeneration, as well as in the reduction of side effects of such procedures.

Example 32

Preparing a Food Supplement in the Form of a Soft Gelatin Capsule Comprising the Claimed Agent The claimed agent according to examples 1-12, 15-23 may be used to fill soft gelatin capsules by means of standard processes. In this respect, a study was conducted of soft gelatin capsule stability when filled with a composition according to example 17 (green coffee bean extract+NIS+ascorbyl palmitate+antioxidant) by the seam welding method. Oval size 10 capsules and oblong size 11 capsules were used, with composition mass of 0.60 g in a capsule. The conducted research demonstrated that capsules are stable over a period of time of at least 12 months. During that time, changes of physical and chemical properties are observed neither in capsule shell, nor in their content.

The described food supplement is recommended for administration of 1 capsule a day for the treatment of dietary deficiencies that adversely affect the organism restoring after having been exposed to harmful factors or physical exertion, and also to enhance efficacy and safety of aggressive cosmetic procedures.

Example 33

Preparing a Food Supplement in the Form of a Hard Gelatin Capsule Comprising the Claimed Agent The claimed agent may be used to produce a food supplement in the form of hard gelatin capsules filled with granulate prepared of a mixture with the following composition:

| Composition according to example 12 (green coffee bean extract + NIS) | 17.5% |
|---|---|
| Absolute ethyl alcohol | 12.7% |
| Ascorbic acid | 17.5% |
| Colloidal anhydrous silicon dioxide | 21.8% |
| Microcrystalline cellulose | 30.5% |

To prepare granulate, ascorbic acid, microcrystalline cellulose and silicon dioxide are loaded into the mixer and stirred to uniformity. In a separate vessel, a composition according to example 12 is mixed with ethyl alcohol, and the obtained solution is slowly added to the dry mixture, continuing stirring at a low rate till a uniform mass for granulation is obtained. Further, wet granulation is carried out by passing the obtained mass through the granulator sieve with holes of 3-5 mm in diameter. The obtained granules are deposited in a thin layer on palettes and dried at 20-35° C. in a drying chamber to complete alcohol removal (mass reduction of about 12.5%). After that, dry granulation is conducted by passing the obtained mass through the granulator sieve with holes of 1-2 mm in diameter. As a result, granulate is obtained with green coffee bean extract content of 5%, which is filled in amounts of 400 mg per capsule in hard gelatin capsules size 0.

The described food supplement is recommended for administration of 2-4 capsules a day for the purpose of making up for dietary deficiencies that adversely affect the organism restoring after having been exposed to harmful factors or physical exertion, and also to enhance efficacy and safety of aggressive cosmetic procedures.

Example 34

Preparing a Food Supplement in the Form of a Tablet Comprising the Claimed Agent To prepare a food supplement in the form of a tablet comprising the claimed agent, a formulation of the following composition is used:

| Composition according to example 17 (green coffee bean extract + NIS + ascorbyl palmitate + antioxidant) | 17.5% |
|---|---|
| Absolute ethyl alcohol | 12.7% |
| Lactose monohydrate | 55.0% |
| Sodium carboxymethyl starch | 0.9% |
| Colloidal anhydrous silicon dioxide | 13.1% |
| Magnesium stearate | 0.9% |

To prepare tablet mass, lactose monohydrate, sodium carboxymethyl starch and silicon dioxide are loaded in the mixer and stirred to uniformity. In a separate vessel, a composition according to example 17 is mixed with ethyl alcohol, and the obtained solution is slowly added to the dry mixture, continuing stirring at a low rate till a uniform mass for granulation is obtained. Further, wet granulation is carried out by passing the obtained mass through the granulator sieve with the size of meshes of 3-5 mm in diameter. The obtained granules are deposited in a thin layer on palettes and dried at 20-35° C. in a drying chamber to complete alcohol removal (mass reduction of about 12.5%). The dried granular material is placed in a homogenizer and ground for 30 minutes. Then magnesium stearate is added, and the mixture is stirred for another 5 min. The obtained tablet mass with a 3% content of green coffee bean extract is used to manufacture oval 500 mg tablets.

The described food supplement is recommended for administration of 2-4 tablets a day for the purpose of making up for dietary deficiencies that adversely affect the organism restoring after having been exposed to harmful factors or physical exertion, and also to enhance efficacy and safety of aggressive cosmetic procedures.

Example 35

Preparing a Foodstuff in the Form of Beverage Comprising the Claimed Agent

Taking into account the ability of the composition to disperse in water with the formation of transparent and weakly opalescent solubilizates, it may be used for the preparation of both transparent and opaque beverages enriched in biologically active substances.

Without limiting the possibility to create foodstuffs and, in particular, beverages with the aid of compositions disclosed herein, a composition of a transparent alcohol-free beverage is provided below, with ingredients shown in mg per 100 ml:

| Composition according to example 23 (comprising: green coffee bean extract - 5 mg, vitamin E - 0.25 mg, vitamin A - 0.025 mg, coenzyme Q10 - 0.25 mg, vitamin C - 5 mg) | 50.00 |
|---|---|
| Niacin | 1.80 |
| Pantothenic acid | 0.60 |
| Vitamin B6 | 0.20 |
| Vitamin B2 | 0.16 |
| Vitamin B1 | 0.14 |
| Folic acid, µg | 20.00 |
| Biotin, µg | 15.00 |

| | |
|---|---|
| Vitamin B12, μg | 0.10 |
| Sweetener (sugar) | 1000.00 |
| Acidity regulator (citric acid) | 200.00 |
| Flavoring agent with coffee flavor | 50.00 |
| Food dye | 30.00 |
| Preservation agent (sodium benzoate) | 20.00 |
| Drinking water | the rest |

To prepare the beverage, all ingredients are dissolved, except composition according to example 23, in the amount of water corresponding to the amount of beverage, and heated to 50° C. The prepared solution is cooled to room temperature, and composition according to example 23 is added thereto. The mixture is stirred till the obtaining of a transparent product.

The described beverage is recommended for administration before, during and after aggressive cosmetic procedures, since it contains nutrient substances necessary for efficient of regenerative processes, including those in the skin, and ensuring resistance thereof to aggressive factors of the environment, among them aggressive cosmetic procedures, and also for consumption for the purpose of making up for dietary deficiencies that adversely affect the organism restoring after having been exposed to harmful factors or physical exertion.

Example 36

Description of Cosmetic Preparation Application Effect for HSP70 Induction (Stimulation of Reparative Processes)

To demonstrate the effect of HSP induction in the skin by means of application of the claimed agent as a component of cosmetic cream, a cream was used prepared as described in example 29. The comparison was made with a cream with the same cream base and the same green coffee bean extract (Svetol) content, said extract being added outside of the claimed composition and without the other components thereof. To control the effect of the additional components of the claimed agent, a cream was used comprising such components, with the cream base according to example 29 and with the addition of the composition according to example 16 prepared without green coffee bean extract (Svetol). To control the effect of manipulations and cream base, a group of animals was used to which cream was applied without the addition of the claimed agent in the form of the cream base according to example 29, i.e. without Phase E.

The research was carried out on BALB/c mice weighing from 20 to 25 g. The animals were held under natural light and free access to water and food (complete balanced diet for laboratory mice and rats). From the skin areas on the back that were undergoing experimental treatment, hair coat was cut directly prior to the first cream application. Cream was applied thrice with a day's interval on an area 1 cm×1 cm in an amount of 0.1 g per cm$^2$, and rubbed in with fingers till complete absorption. Each type of cream was applied to 12 mice.

Following one day after the last application of the creams, half of the animals treated with each type of cream were kept for 1 hour at 42° C., and then all animals were kept at room temperature (23° C.) for another 6 hours. Then the animals were sacrificed by means of cervical dislocation, and the skin areas that had undergone treatment were cut out from the sacrificed animals. The skin flaps were frozen and stored in liquid nitrogen.

On the day of analyses, the samples were unfrozen and homogenized by means of a Polytron homogenizer in PBS chilled on ice comprising a mixture of protease inhibitors, in an amount of 100 mg of tissue per 1 ml of buffer. The obtained homogenate was centrifuged for a period of 20 minutes at 10,000 g to precipitate tissue fragments and cells. In the obtained supernatant, HSP70 content was determined by ELISA, and the obtained value calculated per 1 g of tissue.

Figure 5:
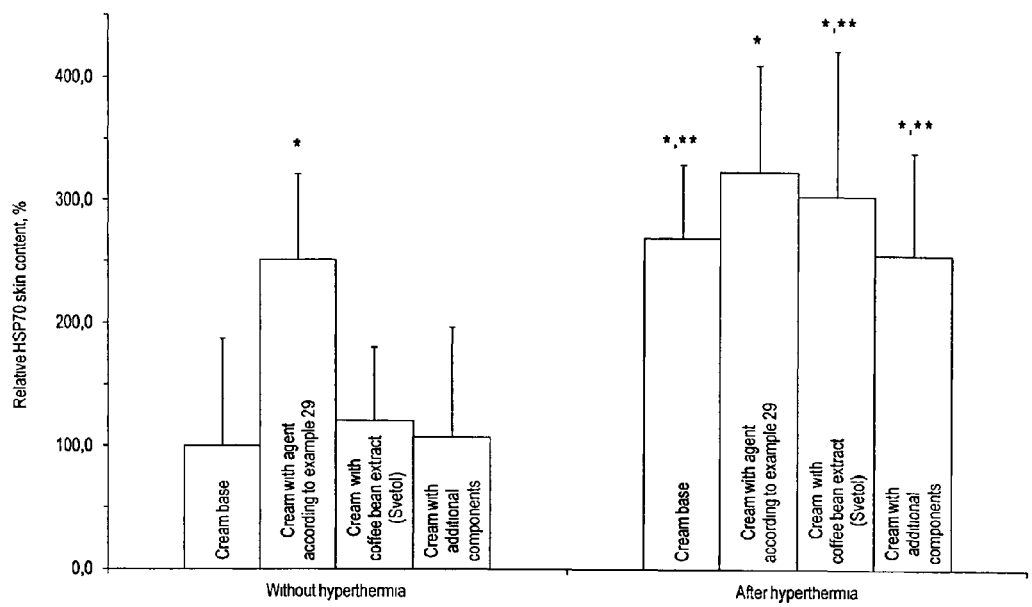
FIG. 5. HSP70 synthesis in mouse skin after treatment with cosmetic cream comprising the agent according to Example 29.

HSP70 synthesis in mouse skin after treatment with cosmetic cream comprising the claimed agent according to example 29 is shown in FIG. 5.

The relative HSP70 content calculates as ratio of absolute content in the skin after specified treatment to the absolute mean HSP70 content in the skin of the mice treated only with the cream base according to example 29 without Phase E. The data shows the mean±standard error of the mean for 6 animals. *–$P<0.05$ in comparison with animals treated with the cream base. **–$P<0.05$ in comparison with animals treated with the same cream, but not subjected to hyperthermia.

The obtained results (FIG. 5) demonstrate the ability of a cosmetic cream comprising the claimed agent to induce HSP70 synthesis independently, without additional exposure to stress, to levels close to those achieved under heat shock. That confirms the ability of the claimed agent to stimulate reparative processes in the skin before it is subjected to stress, which, among other factors, is one of the conditions of reducing undesirable effects during aggressive cosmetic procedures.

Example 37

Description of a method of applying the cosmetic preparation in aggressive cosmetic procedures. Reduction of the time of duration of inflammatory reaction after fractional photothermolysis by means of Fraxel SR 1500 laser during application of the cream according to example 30 comprising the claimed agent, by assessing transepidermal water loss and erythema.

To demonstrate the effect of HSP induction in the skin by means of application of the claimed agent as a component of a cosmetic cream on the intensity of side effects of aggressive cosmetic procedures, cream was used prepared as described in example 30. A comparison was made with cream on the basis of the same cream base and with the identical green coffee bean extract (Svetol) content, such extract being added outside of the claimed composition and without the other components thereof. To control the effect of the additional components of the claimed agent, a cream was used comprising such components, with the cream base according to example 30 and with the addition of the composition according to example 17 prepared without green coffee bean extract (Svetol). To control the effect of manipulations and cream base, a cream was used without the addition of the claimed agent in the form of the cream base according to example 30, i.e. without Phase C.

The study involved 10 volunteers of skin type II-III according to Fitzpatrick scale without dermatologic disorders, who had signed their informed consent to research. Over a period of three days prior to procedures, the cream of the above-described composition was applied on 5 cm×5 cm non-overlapping skin zones of both inner forearms of the test persons in an amount of 0.1 g per 1 cm$^2$. The cream was uniformly distributed over the respective area and rubbed in till complete absorption.

On the following day after the third application of the cream, the test subjects were subjected to the procedure of fractional photothermolysis with the use of Fraxel SR 1500 laser on the treated forearm area, with the engagement of an untreated area of approximately the same size. A mode of treatment with energy of 12 mJ per microthermal zone (MTZ) and density of 2,000 MTZ/cm² was used (8 passes of 250 MTZ/cm² each).

As side effects of laser fractional photothermolysis increased transepidermal water loss (TEWL) and erythema development was studied on skin zones treated with different cream and untreated by any cream. TEWL were measured by Tewameter® TM 300 device, and erythema index by Mexameter® MX 18 device, with the aid of MPA5 multiprobe adapter (Courage & Khazaka Electronic GmbH). During measurements, the devices were located in the center of the treated areas. The described measurements were taken immediately prior to the fractional photothermolysis procedure and following a variety of time periods thereafter.

Figure 6:
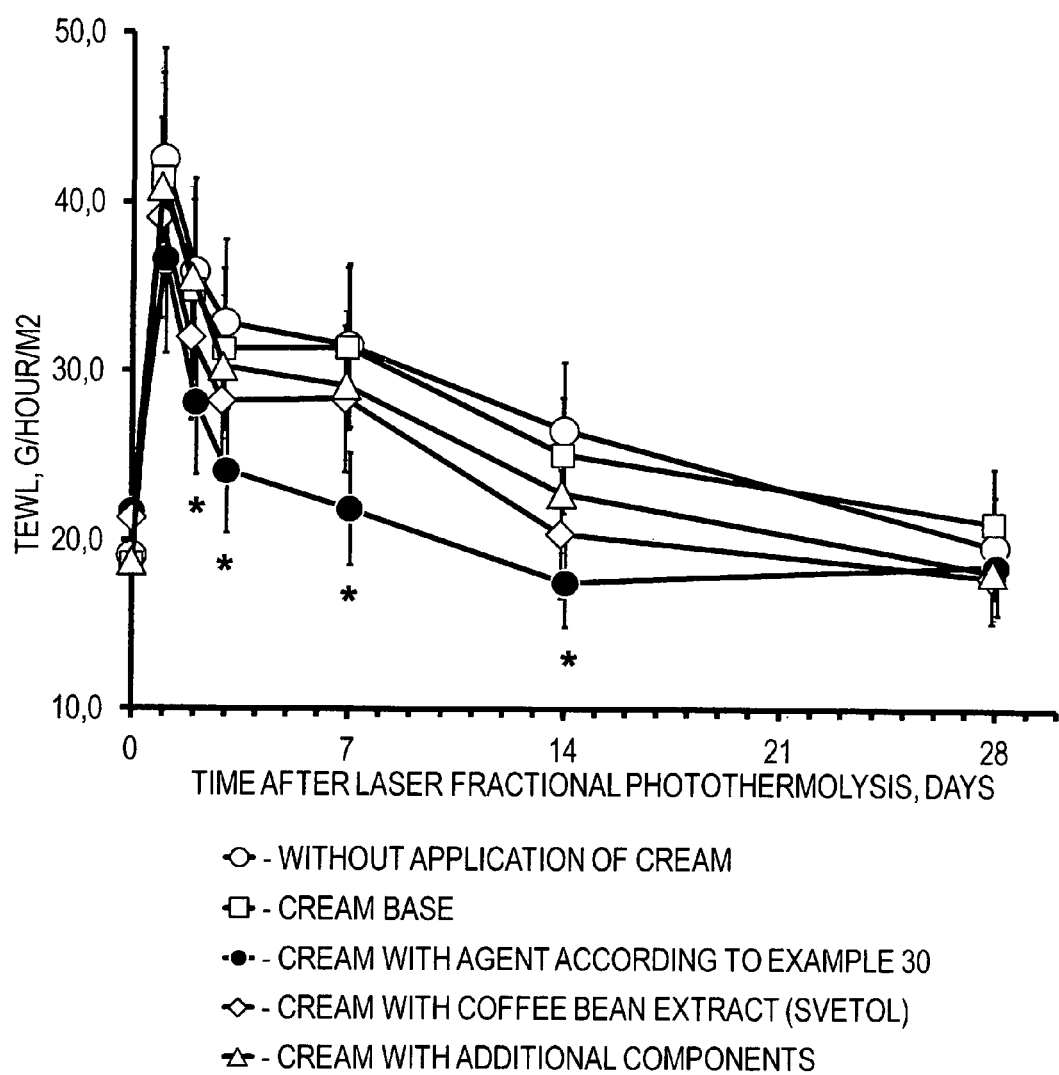
FIG. 6. Transepidermal water loss (TEWL) on skin zones treated with cosmetic creams of different compositions.

TEWL on skin zones treated with cosmetic creams of different compositions is shown in FIG. 6.

The data are shown as the mean±standard deviation. *–$P<0.05$ in comparison of TEWL values on skin zones treated with the cream according to example 30 comprising the claimed agent, with control creams.

Figure 7:
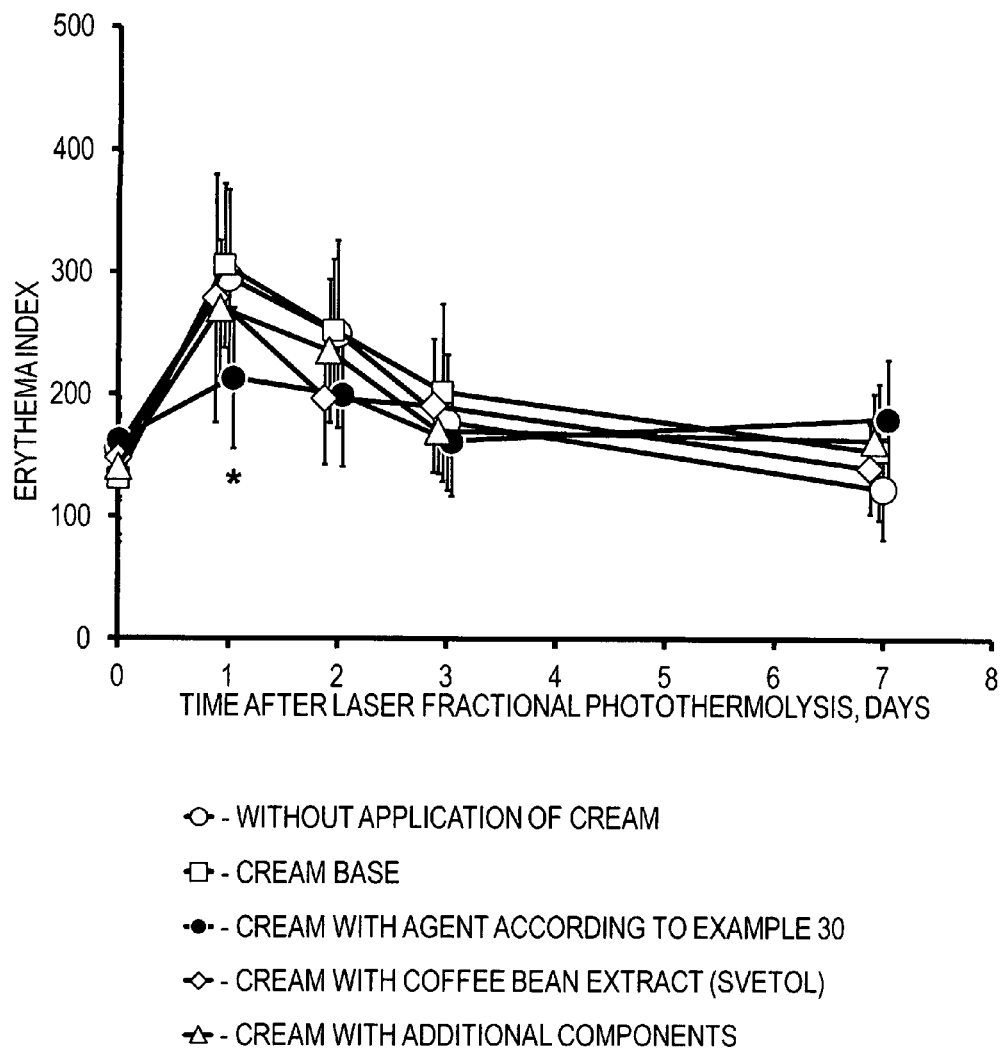
FIG. 7. Erythema indexes on skin zones treated with cosmetic creams of different compositions.

Erythema indexes on skin zones treated with cosmetic creams of different compositions is shown in FIG. 7.

The data are shown as the mean±standard deviation. *–$P<0.05$ in comparison of erythema index values on skin zones treated with the cream according to example 30 comprising the claimed agent, with control creams.

The obtained results demonstrate the ability of the cosmetic cream comprising the claimed agent, to reduce inflammatory reaction symptoms in the skin after laser fractional photothermolysis. It is manifested in reliable reduction of the time of barrier skin function recovery (FIG. 6) and lower erythema intensity (FIG. 7) with prior use of the said cream as compared to other creams under study, including the cream comprising green coffee bean extract (Svetol) as an independent ingredient outside of the claimed agent, for which reduction of side effects was insignificant. It confirms the ability of the claimed agent to effectively reduce the intensity of undesirable side effects during aggressive cosmetic procedures by way of prior stimulation of reparative processes in the skin.

Example 38

Description of a method of using dietary supplements to stimulate reparative processes during physical exercise. The reduction of the degree of damage to muscular cells after physical exercise with by means of consumption of food supplement according to example 33 comprising the claimed agent.

The study involved 18 healthy male volunteers aged 19-25 not actively involved in any sport or any other kind of special physical training, having no contra-indications to performing strenuous physical works, and who had given their informed consent to research. Over a period of 30 days, six test subjects took 2 capsules a day of the food supplement according to example 33 comprising the claimed agent. Another group of six test persons took 2 capsules a day comprising the same amount of green coffee bean extract (Svetol) added outside of the claimed agent and without the other components thereof. The third group of six test subjects took 2 capsules per day of placebo without green coffee bean extract (Svetol), comprising additional substances used to prepare the food supplement according to example 33, with the addition of Polysorbate 80 used to prepare the composition according to example 12 in the respective amount.

Following one and two days after the last administration of the food supplement, the test subjects performed, for a period of 90 minutes, exercise on cycle ergometer (BodyGuard, Sandnes, Norway) at 60 rpm and 1.5 kgf.

Immediately before the first exercise and directly after the second, vein blood samples were collected from the test subjects and blood serum obtained after the formation of a blood clot over a period of 30 minutes at room temperature by means of centrifuging at 3,000 g for 10 minutes. The obtained serum samples were frozen and stored till analyses at −80° C. Creatine kinase activity in serum was determined with the use of a standard reagent set at 37° C. The effect of the consumption of the food supplement according to example 33 comprising the claimed agent on the change of creatine kinase activity in the blood of volunteers after hard physical activity is shown in table 3.

TABLE 3

| Preparation administered to a group of volunteers | Creatine kinase activity in volunteer blood serum, IU/l | |
|---|---|---|
| | Before physical exercise | After physical exercise |
| Capsules of food supplement according to example 33 containing claimed agent | 107.3 ± 68.5 | 175.3 ± 74.2 *, ** |
| Capsules with green coffee bean extract (Svetol) without claimed agent | 115.8 ± 75.2 | 258.4 ± 87.8 * |
| Placebo | 98.5 ± 57.4 | 271.8 ± 85.1 * |

Notes.
1. Data are expresses as the mean plus/minus standard error of the mean.
2. * $P < 0.05$ in comparison with values before physical activity in the group.
** $P < 0.05$ in comparison with control groups after physical activity.

No deviations were observed in the state of volunteers taking the preparations under study. That said, the intake of food supplements comprising the claimed agent results in lesser creatine kinase activity growth in the blood of test subjects of the respective group compared to the other groups (table 3). Since creatine kinase activity growth in the blood is a result of muscular cell damage under strenuous physical activity, the obtained result demonstrates the ability of the claimed agent to increase the organism's resistance to exercise stress, as opposed to green coffee bean extract, a component of the claimed agent, acting independently.

What is claimed is:
1. An agent for heat shock protein induction in human and animal cells comprising:
   a phenolic compound or a mixture of phenolic compounds, wherein the phenolic compound or the mixture of phenolic compounds is/are selected from the group consisting of chlorogenic acid, ferulic acid, caffeic acid, curcumin and a phenylethyl ester of caffeic acid, and
   a nonionic surface-active agent, or a mixture of nonionic surface-active agents, wherein the nonionic surface-active agent, or the mixture of nonionic surface-active agents is/are in an amount of at least 75 weight %.
2. The agent according to claim 1, wherein the mixture of phenolic compounds is an extract from a raw material of a plant or animal origin.
3. The agent according to claim 2, wherein the extract of a plant origin is a coffee bean extract.

4. The agent according to claim 1, wherein the nonionic surface-active agent or the mixture of nonionic surface-active agents has a hydrophilic-lipophilic balance (HLB) ranging from 10 to 18.

5. The agent according to claim 4, wherein the nonionic surface-active agent or the mixture of nonionic surface-active agents is/are selected from the group consisting of Polysorbate 20, Polysorbate 40, Polysorbate 60, Polysorbate 80, PEG-40 hydrated castor oil, 35- polyoxyethylated castor oil and PEG- 15 hydroxystearate.

6. A cosmetic preparation for stimulating reparative processes, which comprises the agent according to claim 1.

7. The cosmetic preparation according to claim 6, wherein the agent according to claim 1 is in an amount of at least 0.1 weight %.

8. The cosmetic preparation according to claim 6, further comprising ascorbic acid or a derivative thereof in an amount of 0.01-20 weight %.

9. The cosmetic preparation according to claim 6, further comprising a natural or synthetic fat-soluble antioxidant or a mixture of such antioxidants in an amount of 0.01-2 weight %.

10. The cosmetic preparation according to claim 9, wherein the natural or synthetic fat-soluble antioxidant, or the mixture of such antioxidants is/are selected from the group consisting of tocopherol, carotene, retinol, lutein, lycopene, and ubiquinone.

11. The cosmetic preparation according to claim 6, wherein the cosmetic preparation is in the form of an emulsion, a cream, milk, a balm, an ointment, a gel, a shampoo, a tonic, a lotion, or a pomade.

12. A method of reducing side effects of a cosmetic procedure, comprising:
performing the cosmetic procedure on an anatomical region of a subject; and
applying, on the anatomical region of the subject, the cosmetic preparation according to claim 6, wherein the cosmetic preparation is applied before and/or during and/or after the procedure.

13. A food supplement comprising the agent according to claim 1.

14. The food supplement according to claim 13, wherein the agent according to clause 1 is in an amount of at least 1 weight %.

15. The food supplement according to claim 13, further comprising ascorbic acid in an amount of 0.01-20 weight %.

16. The food supplement according to claim 13, further comprising a natural or synthetic fat-soluble antioxidant or a mixture of such antioxidants in an amount of 0.01-2 weight %.

17. The food supplement according to claim 16, wherein the natural or synthetic fat-soluble antioxidant, or the mixture of such antioxidants is/are selected from the group consisting of tocopherol, carotene, retinol, lutein, lycopene and ubiquinone and derivatives thereof.

18. The food supplement according to claim 13, wherein the food supplement is in the form of capsules, tablets, powder, granules, microspheres, pills, candy, suspension, emulsion, or a soluble form.

19. A foodstuff, comprising the agent according to claim 1.

20. The foodstuff according to claim 19, comprising the agent according to clause 1 in an amount of at least 0.001 weight %.

21. The foodstuff according to claim 19, comprising ascorbic acid in an amount of 0.01-20 weight %.

22. The foodstuff according to claim 19, further comprising a natural or synthetic fat-soluble antioxidant or a mixture of such antioxidants in an amount of 0.01-2 weight %.

23. The foodstuff according to claim 22, wherein the natural or synthetic fat-soluble antioxidant or the mixture of such antioxidants is/are selected from the group consisting of tocopherol, carotene, retinol, lutein, lycopene and ubiquinone.

24. The foodstuff according to claim 19, wherein the foodstuff is a ready-for-use product, instant food, food concentrate or beverage.

25. The method of claim 22, wherein the cosmetic procedure is conducted concurrently with the consumption of a food supplement and/or a foodstuff before and/or during and/or after the procedure, wherein the food supplement and/or the foodstuff comprise an agent according to claim 1.

26. The agent according to claim 2, wherein the extract of a plant origin is a green coffee bean extract.

27. The cosmetic preparation according to claim 6, wherein the agent according to claim 1 is in an amount of from 0.5 to 5 weight %.

28. The foodstuff according to claim 19, comprising the agent according to clause 1 in an amount of 0.01 to 0.5 weight %.

* * * * *